US010238471B2

(12) United States Patent
Chan

(10) Patent No.: US 10,238,471 B2
(45) Date of Patent: Mar. 26, 2019

(54) DENTAL IMPLANT ASSEMBLY AND ABUTMENT THEREOF

(71) Applicant: Chia-Yi Chan, New Taipei (TW)

(72) Inventor: Chia-Yi Chan, New Taipei (TW)

( * ) Notice: Subject to any disclaimer, the term of this patent is extended or adjusted under 35 U.S.C. 154(b) by 27 days.

(21) Appl. No.: 15/386,266

(22) Filed: Dec. 21, 2016

(65) Prior Publication Data

US 2017/0181814 A1 Jun. 29, 2017

(30) Foreign Application Priority Data

Dec. 25, 2015 (TW) ............................ 104220829 U
Oct. 21, 2016 (TW) ............................ 105216103 U

(51) Int. Cl.
*A61C 8/00* (2006.01)

(52) U.S. Cl.
CPC ............ *A61C 8/0057* (2013.01); *A61C 8/006* (2013.01); *A61C 8/0068* (2013.01); *A61C 8/0069* (2013.01)

(58) Field of Classification Search
CPC ...................................... A61C 8/0048–8/0078
USPC .................................................. 433/172–176
See application file for complete search history.

(56) References Cited

U.S. PATENT DOCUMENTS 5,302,125 A * 4/1994 Kownacki ............ A61C 8/0048 433/172
5,782,918 A * 7/1998 Klardie .................. A61C 8/005 433/172
9,017,075 B1 * 4/2015 Tsai ..................... A61C 8/0022 433/174
9,333,057 B2 * 5/2016 Benzon ................ A61C 8/0053
2002/0142266 A1 * 10/2002 Rogers ................. A61C 8/0001 433/173
2006/0121416 A1 * 6/2006 Engman ............... A61C 8/0001 433/173
2009/0246733 A1 * 10/2009 Auderset ................ A61C 8/005 433/173
2009/0253098 A1 * 10/2009 Whipple ............. A61C 8/0087 433/174
2010/0062395 A1 * 3/2010 Bar Shalom ........... A61C 8/005 433/173
2010/0291507 A1 * 11/2010 Abdelgany ............ A61C 8/005 433/174

(Continued)

*Primary Examiner* — Matthew M Nelson
(74) *Attorney, Agent, or Firm* — Muncy, Geissler, Olds & Lowe, P.C.

(57) ABSTRACT

A dental implant assembly includes an implant, an abutment, and a fixing element. The implant is placed in the alveolar bone. The abutment is assembled to the implant and includes a tapered position-restricting part and an elastic pressing part. The tapered position-restricting part has an abutment fixing channel substantially matching the tapered position-restricting outer wall of the tapered position-restricting trench. The elastic pressing part includes the elastic pressing structures extended from the tapered position-restricting part. The fixing element includes the fixing head and the fixing rod extended from the fixing head. A tolerance allowable gap is formed between the abutment fixing channel and the fixing rod. As the abutment is assembled to the implant, the elastic pressing structures press against the position-restricting wall first to hinder the relative rotation therebetween; when an offset error exists, the tolerance allowable gap allows the fixing rod to penetrate the abutment fixing channel.

11 Claims, 12 Drawing Sheets

(56) References Cited

U.S. PATENT DOCUMENTS

| | | | | | |
|---|---|---|---|---|---|
| 2011/0171599 | A1* | 7/2011 | Seo | A61C 8/005 | 433/173 |
| 2014/0242545 | A1* | 8/2014 | Brun | A61C 8/0001 | 433/173 |
| 2015/0230888 | A1* | 8/2015 | Porter | A61C 8/006 | 433/201.1 |
| 2016/0081773 | A1* | 3/2016 | Kim | A61C 8/0056 | 433/170 |

* cited by examiner

DENTAL IMPLANT ASSEMBLY AND ABUTMENT THEREOF

This application claims the benefit of Taiwan Patent Application Serial No. 104220829, filed Dec. 25, 2015 and Serial No. 105216103, filed Oct. 21, 2016, the subject matter of which are incorporated herein by reference.

BACKGROUND OF INVENTION

1. Field of the Invention

The present invention is related to a dental implant assembly and an abutment thereof, and more particularly is related to a dental implant assembly, which uses an elastic pressing structure to prevent relative rotation between the implant and the abutment and adopts the tolerance allowable gap between the fixing rod and the abutment fixing channel to overcome the interference issue due to offset errors between the implant and the abutment, and an abutment thereof.

2. Description of the Prior Art

The history of dental implant technology can be traced back to Medieval. The ancient Egyptian and South American civilization replace the missing teeth using carved ivory and wood. Starting from the 19th century, people stated to use different materials as dental implant, such as gold, platinum, ceramic, and Co—Cr—Mo alloy. Until the end of 20th century, dental implant technology was well developed with over 200 different dental implant assemblys.

FIG. 1 is a cross-section view of a dental implant assembly provided in accordance with the conventional technology. As shown, during the conventional dental implant surgery using the dental implant assembly PA1, an implant is placed in an alveolar bone PA2 (shown in FIG. 3) first. After a few months until the bone heals and the implant PA11 is firmly fixed in the alveolar bone PA2, the dentist will screw an abutment PA11 into a screw hole PA111 of the implant PA11 using a screw PA13 penetrating the abutment channel PA121 of the abutment PA12, and also decide the shape of the crown to be fixed on the abutment PA12 according to the dental structure.

However, because the dental implant assembly PA1 is a assembly with precision components, a slight difference may lead to a huge problem. FIG. 2 is a cross-section view showing a dental implant assembly having an abutment channel with tolerance provided in accordance with the conventional technology. As shown, if there is any angular or positional error happened in the abutment channel PA121' of the abutment PA12' during manufacturing, it is common to find that the screw PA13 passing through the abutment channel PA121' cannot be aligned with the screw hole PA111 of the implant PA11, such that the abutment PA12' cannot be fixed to the implant PA11 by using the screw PA13.

FIG. 3 is a cross-section view showing the dental implant assembly with three abutments as a unit screw-fixed on three different implants with errors in accordance with a conventional technology. As shown, when a dental implant surgery with multiple adjacent teeth is needed, the dentist may place three implants PA11, PA11*a*, PA11*b* into the alveolar bone PA2 first. After the healing period, the second procedure takes place to screw-fix the three abutments PA12, PA12*a*, PA12*b* jointed by the dental bridge to the implants PA11, PA11*a*, PA11*b*.

It is common for the dentist to do the dental implant surgery using a guiding plate to place the implants PA11, PA11*a*, PA11*b* into the alveolar bone PA2. However, even with the assistance of tools, human errors, such as the position error or the angular error with 1 to 2 degrees during the implant placement process, are still unpreventable, such that the implants PA11, PA11*a*, PA11*b* may be unparalleled with each other when placed into the alveolar bone PA2. Meanwhile, the relative position and angle between the abutments PA12, PA12*a*, PA12*b* are not adjustable because these abutments PA12, PA12*a*, PA12*b* are jointed by the dental bridge PA3. Under such restriction, it would be difficult to screw-fix the abutments PA12, PA12*a*, PA12*b* jointed by the dental bridge PA3 as a unit on the implants PA11, PA11*a*, PA11*b* simultaneously due to the misalignment among the implants PA11, PA11*a*, PA11*b* when placing the artificial teeth, and would be also difficult to remove the screw-fixed abutments PA12, PA12*a*, PA12*b* jointed by the dental bridge PA3 as a unit from the implants PA11, PA11*a*, PA11*b*.

SUMMARY OF THE INVENTION

In view of the conventional art, which may encounter the difficulty of fixing the screw into the implant screw hole as the abutment channel has error, and the problems of screwing multiple abutments jointed by the dental bridge as one unit into multiple implants which are screw-fixed in the alveolar bone or removing such abutments from the implants due to the misalignment issue among the individual implants.

In order to resolve the problem of the conventional technology, a dental implant assembly is provided in accordance with the present invention. The dental implant assembly is placed in in an alveolar bone and comprises an implant, an abutment, and a fixing element. The implant is placed in the alveolar bone, and has a tapered position-restricting trench surrounded by a position-restricting wall. The tapered position-restricting trench has an implant central axis.

The abutment is assembled to the implant, and comprises a tapered position-restricting part and an elastic pressing part. The tapered position-restricting part has an abutment fixing channel extending along an abutment central axis, and has a tapered position-restricting outer wall which is configured to substantially engage with the tapered position-restricting trench. A tilted position-restricting angle is formed between the tapered position-restricting outer wall and the abutment central axis. The elastic pressing part comprises a plurality of elastic pressing structures extended from the tapered position-restricting part. A tilted pressing angle formed between the elastic pressing structures and the abutment central axis is smaller than the tilted position-restricting angle.

The fixing element comprises a fixing head and a fixing rod. The fixing head has a head diameter. The fixing rod is extended from the fixing head and is configured to penetrate the abutment fixing channel to connect the implant so as to have the abutment fixed to the implant. The fixing rod has a rod diameter.

Wherein the abutment fixing channel has a channel diameter, the fixing head diameter is greater than the channel diameter, and the channel diameter is greater than the rod diameter to compose a tolerance allowable gap between the abutment fixing channel and the fixing rod. When the abutment is assembled to the implant, the elastic pressing structures press against the position-restricting walls before the tapered position-restricting part because the tilted pressing angle is smaller than the tilted position-restricting angle, such that the elastic pressing structures are elastically deformed to hinder relative rotation between the abutment and the implant. When an offset error existed between the implant central axis and the abutment central axis, the fixing rod penetrates the abutment fixing channel to connect the implant by using the tolerance allowable gap.

In accordance with an embodiment of the present invention, the implant further comprises an implant fixing hole formed from the tapered position-restricting trench extended along the implant central axis, and the fixing rod is fixed in the fixing hole.

In accordance with an embodiment of the present invention, the fixing rod has a thread section at one end thereof away from the fixing head, the implant fixing hole is a screw hole, and the fixing element is screw-fixed to the implant fixing hole by using the thread section.

In accordance with an embodiment of the present invention, the implant further has an implant outer thread section, which is utilized to have the implant screw-fixed to the alveolar bone.

In accordance with an embodiment of the present invention, the elastic pressing part further comprises a plurality of end elastic pressing structures connected to one end of the elastic pressing structures respectively.

In accordance with an embodiment of the present invention, a tilted end structure angle formed between the end elastic pressing structure and the abutment central axis is greater than the tilted pressing angle.

In accordance with an embodiment of the present invention, wherein the channel diameter is ranged from 1.05 to 1.3 times the rod diameter.

In accordance with an embodiment of the present invention, the elastic pressing structures are a plurality of elastic pressing plates spaced apart from each other.

In accordance with an embodiment of the present invention, the position-restricting wall further comprises a tapered wall portion and a pressed portion. The tapered wall portion substantially matches the tapered position-restricting part so as to position and locate the tapered position-restricting part. The pressed portion receives the pressing by the elastic pressing structure. A pressed angle formed between the pressed portion and the implant central axis is greater than the tilted pressing angle.

In accordance with an embodiment of the present invention, the tapered wall portion is a cone-shaped position-restricting wall or a polygon-shaped position-restricting wall, and the tapered position-restricting part matching the tapered wall portion is a cone structure or a polygonal pyramid structure.

In accordance with an embodiment of the present invention, the tapered position-restricting trench is a tapered polygonal trench, and the tapered position-restricting part is a tapered polygonal position-restricting part.

Moreover, in order to resolve the problem of the conventional technology, an abutment for a dental implant assembly is provided in accordance with the present invention. The abutment is assembled to an implant of a dental implant assembly, which is placed in the alveolar bone and has a tapered position-restricting trench surrounded by a position-restricting wall. The tapered position-restricting trench has an implant central axis. The abutment comprises a tapered position-restricting part and an elastic pressing part. The tapered position-restricting part has an abutment fixing channel extending along an abutment central axis, and has an tapered position-restricting outer wall which is configured to substantially engage with the tapered position-restricting trench. A tilted position-restricting angle is formed between the tapered position-restricting outer wall and the abutment central axis.

The elastic pressing part comprises a plurality of elastic pressing structures extended from the tapered position-restricting part, and a tilted pressing angle formed between the elastic pressing structures and the abutment central axis is smaller than the tilted position-restricting angle. A fixing element is utilized to penetrate the abutment fixing channel to fix the abutment to the implant. When the abutment is assembled to the implant, the elastic pressing structures press against the position-restricting walls before the tapered position-restricting part because the tilted pressing angle is smaller than the tilted position-restricting angle, such that the elastic pressing structures are elastically deformed to hinder relative rotation between the abutment and the implant.

In accordance with an embodiment of the present invention, the elastic pressing part further comprises a plurality of end elastic pressing structures connected to one end of the elastic pressing structures respectively.

In accordance with an embodiment of the present invention, a tilted end structure angle formed between the end elastic pressing structure and the abutment central axis is greater than the tilted pressing angle.

In accordance with an embodiment of the present invention, the elastic pressing structures are a plurality of elastic pressing plates spaced apart from each other.

In accordance with an embodiment of the present invention, the tapered position-restricting trench is a tapered polygonal position-restricting trench, and the tapered position-restricting part is a tapered polygonal position-restricting part.

In sum, the dental implant assembly provided in the present invention features the abutment with a plurality of elastic pressing structures, which is capable to hinder the relative rotation between the abutment and the implant by using the friction force between the elastic pressing structures and the position-restricting wall. In addition, with the help of the end pressing structures, the relative rotation between the abutment and the implant can be prevented more effectively. Moreover, the abutment has an abutment fixing channel extending along the abutment central axis which has a channel diameter greater than the rod diameter such that a tolerance allowable gap would be formed between the abutment fixing channel and the fixing rod. Thereby, even with some error happened in the abutment fixing channel, the fixing element is still able to be fixed to the implant successfully.

In contrast with the conventional technology, the dental implant assembly provided in the present invention is capable to resolve the problems of the conventional technology, which include the difficulty of fixing the screw into the implant screw hole as the abutment channel has error, and the difficulties of screwing multiple abutments jointed by the dental bridge as an unit into multiple implants screw-fixed in the alveolar bone or removing such abutments from the implants due to the misalignment issue between the individual implants, by using the tolerance allowable gap between the fixing channel and the fixing rod. Additionally, the dental implant assembly provided in the present invention can hinder the relative rotation between the abutment and the implant by using the elastic pressing structure.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
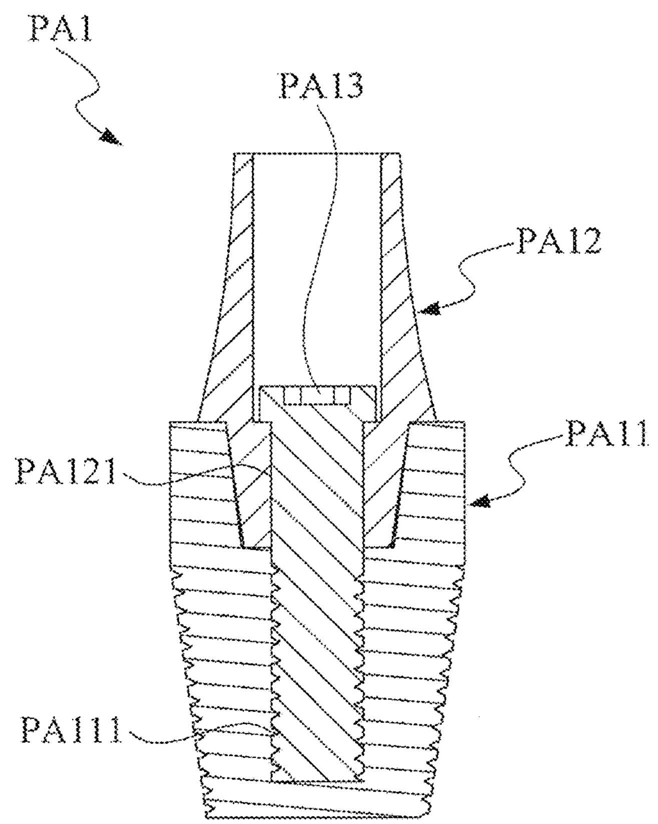
FIG. 1 is a cross-section view of a dental implant assembly provided in accordance with a conventional technology.
Figure 2:
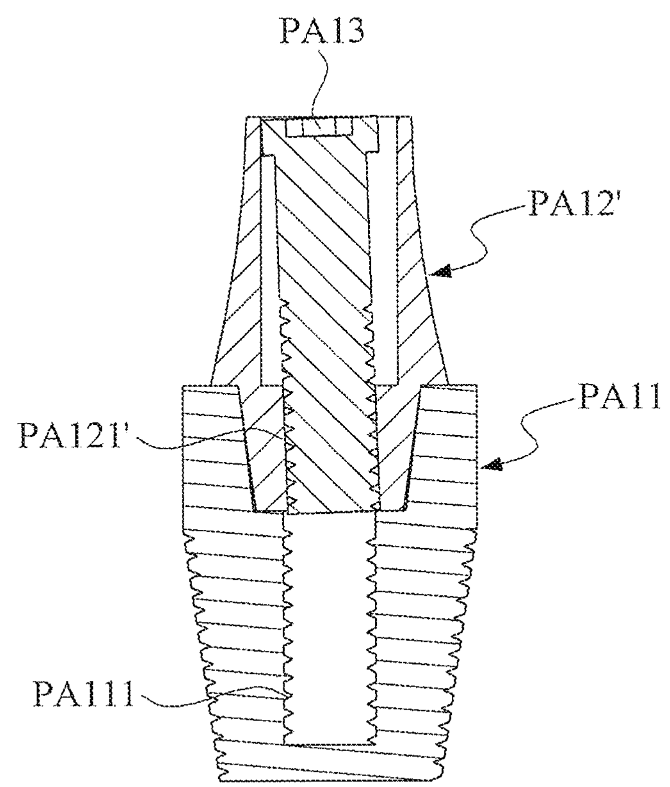
FIG. 2 is a cross-section view of a dental implant assembly having an abutment channel with tolerance provided in accordance with the conventional technology.
Figure 3:
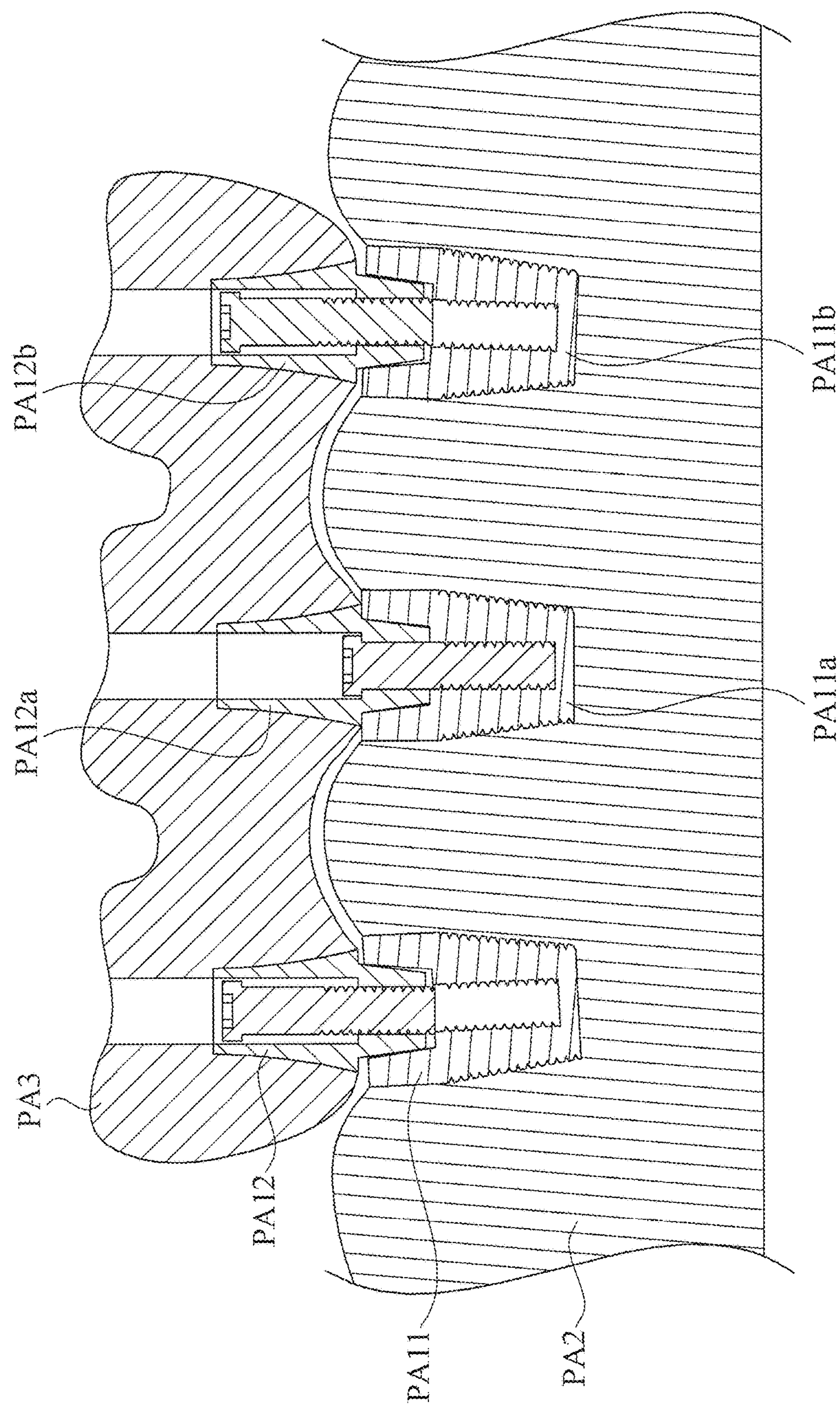
FIG. 3 is a cross-section view showing the dental implant assembly with three abutments as one unit screw-fixed on three different implants with errors in accordance with a conventional technology.
Figure 4:
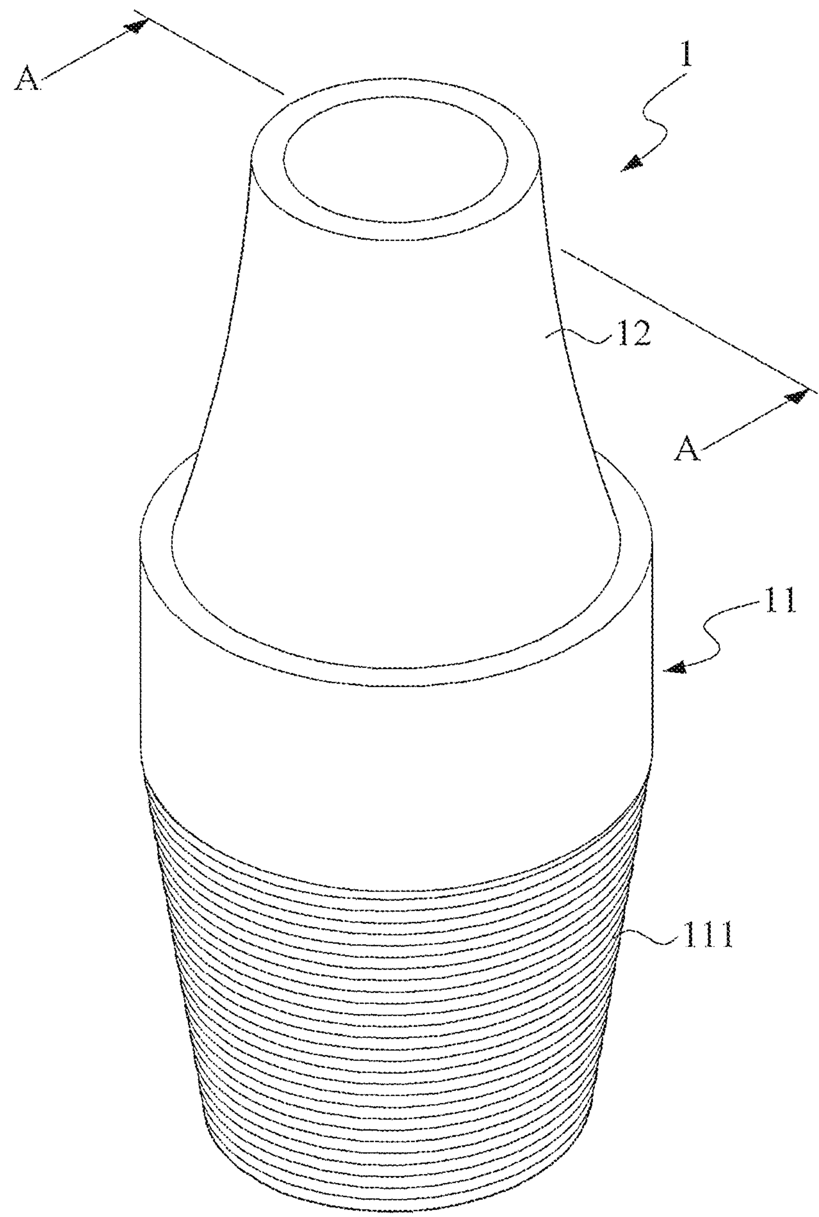
FIG. 4 is a 3D schematic view of the dental implant assembly provided in accordance with first embodiment of the present invention.
Figure 5:
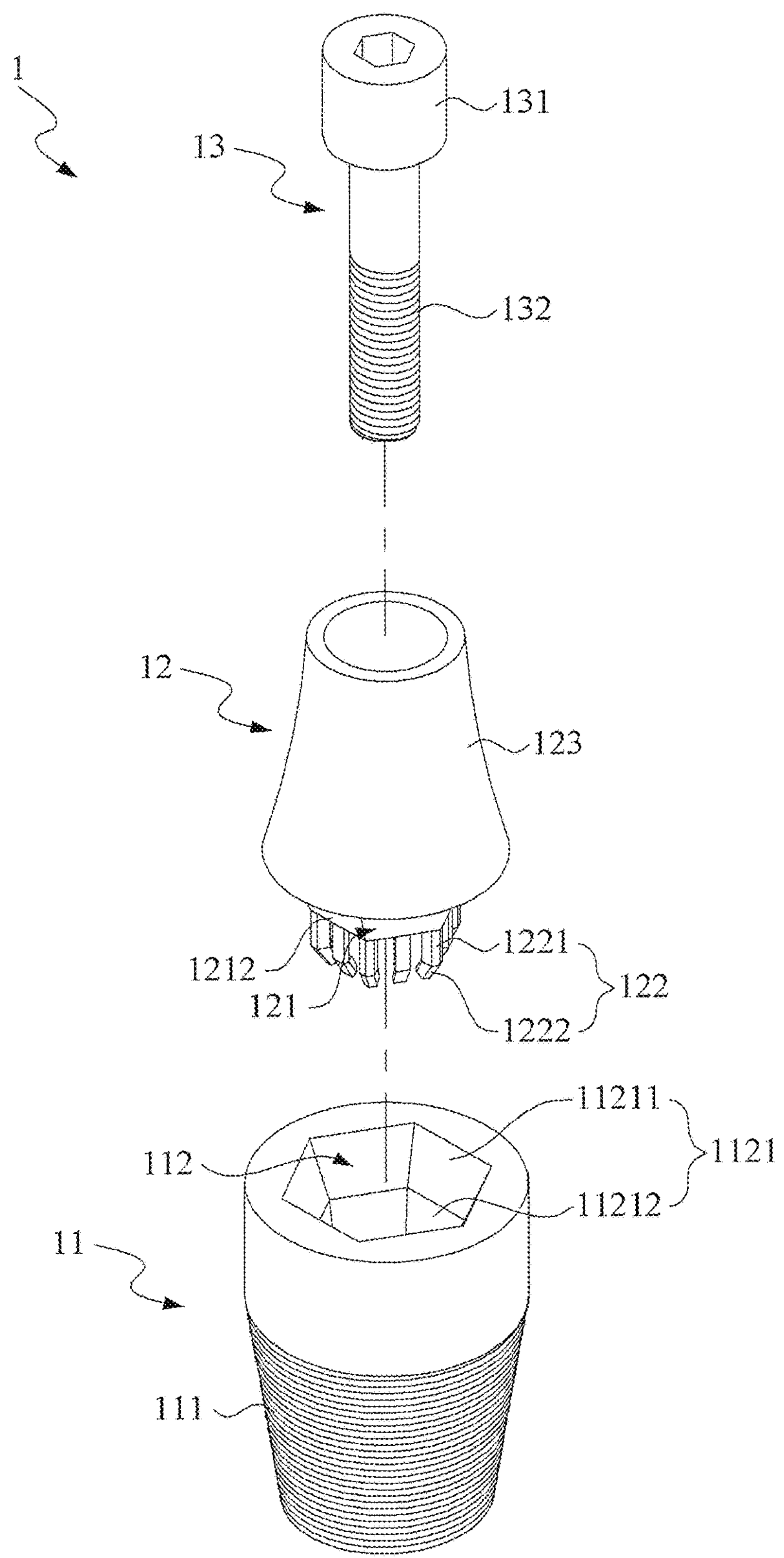
FIG. 5 is a 3D explosive view of the dental implant assembly provided in accordance with the first embodiment of the present invention.
Figure 6:
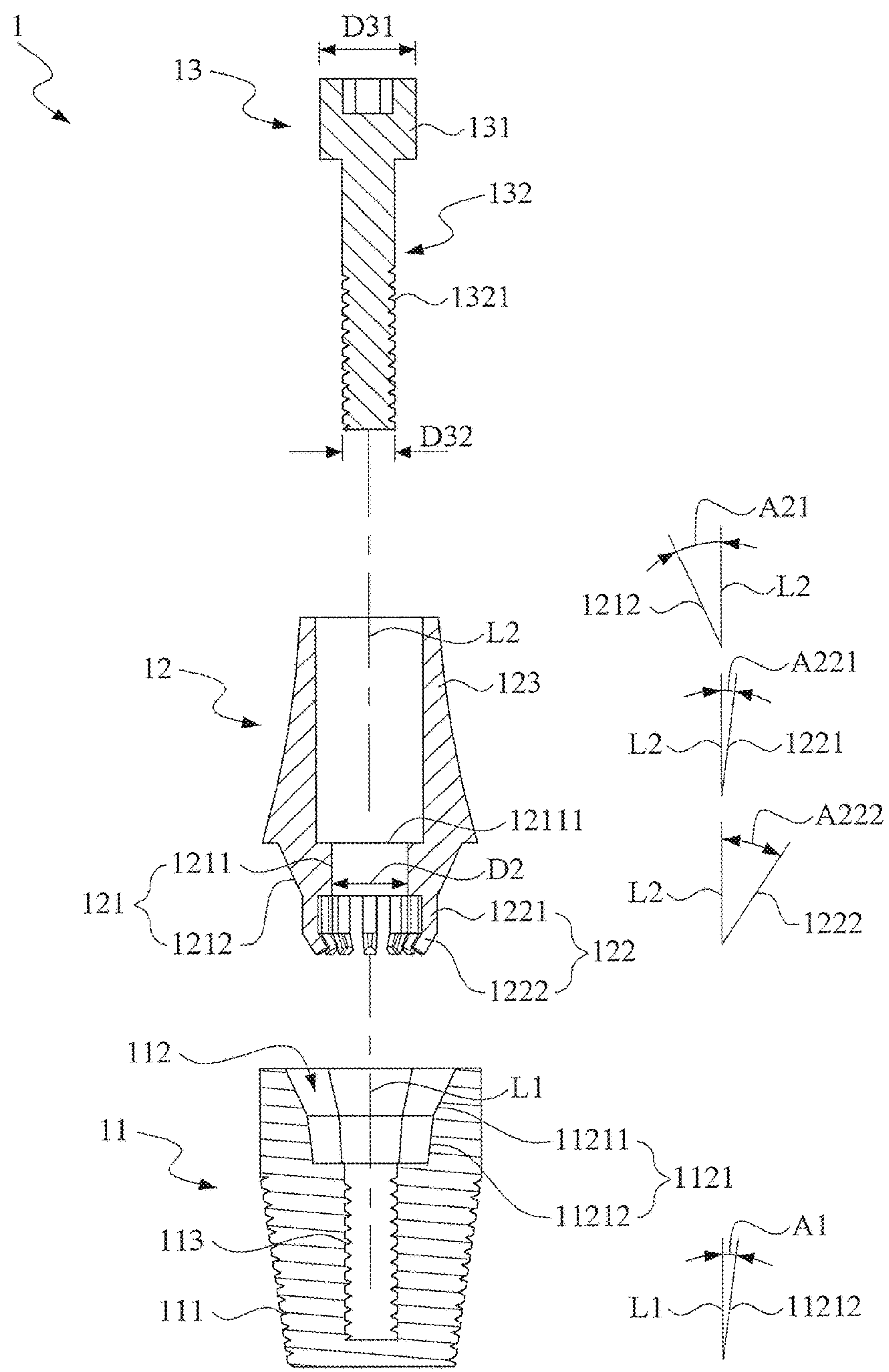
FIG. 6 is a cross-section view along the cross-section A-A of the dental implant assembly provided in accordance with the first embodiment of the present invention.

Please refer to FIGS. 4 to 6, wherein FIG. 4 is a 3D schematic view of the dental implant assembly provided in accordance with first embodiment of the present invention; FIG. 5 is a 3D explosive view of the dental implant assembly provided in accordance with the first embodiment of the present invention; and FIG. 6 is a cross-section view along the cross-section A-A of the dental implant assembly provided in accordance with the first embodiment of the present invention. As shown, the dental implant assembly 1 provided in the present invention is located on an alveolar bone 2 (shown in FIG. 11) and includes an implant 11, an abutment 12, and a fixing element 13.

The implant 11 has an implant outer thread section 111, which is utilized to have the implant 11 screw-fixed to the alveolar bone 2. The implant 11 also has a tapered position-restricting trench 112 surrounded by a position-restricting wall 1121. The tapered position-restricting trench 112 has an implant central axis L1. Preferably, the tapered position-restricting trench 112 is a tapered polygonal position-restricting trench, such as the tapered hexagonal position-restricting trench in the first embodiment. The tapered polygonal position-restricting trench can also be the tapered pentagonal position-restricting trench or the tapered octagonal position-restricting trench for example. It is understood that there are various embodiments regarding the shape of the position-restricting trench, which is not repeated here.

The position-restricting wall 1121 comprises a tapered wall portion 11211 and a pressed portion 11212. The tapered wall portion 11211 is a polygon-shaped position-restricting wall (e.g. a hexagon-shaped position-restricting wall). The polygon-shaped position-restricting wall can be replaced by a cone-shaped position-restricting wall according to the need in practice. A pressed angle A1 is formed between the pressed portion 11212 and the implant central axis L1. In addition, the implant 11 further has an implant fixing hole 113 formed from the tapered position-restricting trench 112 extended along the implant central axis L1, and the implant fixing hole 113 is a screw hole.

The abutment 12 is configured to be assembled to the implant 11 and comprises a tapered position-restricting part 121, an elastic pressing part 122, and a crown setting part 123. The tapered position-restricting part 121 has an abutment fixing channel 1211 extending along an abutment central axis L2, and the abutment fixing channel 1211 has a channel diameter D2. It is noted that the tapered wall portion 11211 substantially matches the tapered position-restricting part 121 so as to have the tapered position-restricting part 121 positioned and located by the tapered wall portion 11211 because the tapered position-restricting part 121 has a tapered position-restricting outer wall 1212 substantially matches the tapered position-restricting trench 112.

For matching the tapered polygonal position-restricting trench and the tapered wall portion 11211, the tapered position-restricting part 121 is a tapered polygon-shaped position-restricting part with a polygonal pyramid structure or a tapered cone-shaped position-restricting part with a cone structure. The engagement between the tapered polygonal position-restricting trench and the tapered polygon-shaped position-restricting part may prevent the relative rotation between the abutment 12 and the implant 11. In the first embodiment, the tapered polygon-shaped position-restricting part is a tapered hexagon-shaped position-restricting part. The tapered polygon-shaped position-restricting part can also be the tapered pentagon-shaped position-restricting part or the tapered octagon-shaped position-restricting part for example. It is understood that there are various embodiments regarding the shape of the position-restricting part, which is not repeated here. In addition, a tilted position-restricting angle A21 is formed between the tapered position-restricting outer wall 1212 and the abutment central axis L2.

The elastic pressing part 122 comprises a plurality of elastic pressing structures 1221 extended from the tapered position-restricting part 121, and a plurality of end elastic pressing structures 1222 connected to one end of the elastic pressing structures 1221 respectively. The elastic pressing structures 1221 are individual elastic pressing plates spaced apart from each other. The end elastic pressing structures 1222 are utilized for increasing the friction force between the abutment 12 and the implant 11 so as to prevent the relative rotation between the abutment 12 and the implant 11.

A tilted pressing angle A221 formed between the elastic pressing structures 1221 and the abutment central axis L2 is smaller than the tilted position-restricting angle A21. In FIG. 6, the tilted pressing angle A221 is the angle between the abutment central axis L2 and the outer wall of the elastic pressing structures 1221. In detail, the tilted pressed angle A1 is greater than the tilted pressing angle A221 so as to have the elastic pressing structures 1221 press against the pressed portion 11212. In addition, a tilted end structure angle A222 is formed between the end elastic pressing structure 1222 and the abutment central axis L2, and the tilted end structure angle A222 is greater than the tilted pressing angle A221. Therefore, the end elastic pressing structures 1222 may possess the function of guiding the abutment 12 into the tapered position-restricting trench 112. In FIG. 6, the tilted end structure angle A222 is the angle between the abutment central axis L2 and the outer wall of the end elastic pressing structure 1222. In addition, the crown setting part 123 is extended from the end of the tapered position-restricting part 121 opposite to the elastic pressing part 122.

The fixing element 13 includes a fixing head 131 and a fixing rod 132. The fixing head 131 has a head diameter D31, which is greater than the channel diameter D2 so as to prevent the fixing head 131 from moving into the abutment fixing channel 1211 and have the fixing head 131 locked at a fixing channel inlet 12111 of the abutment fixing channel 1211.

The fixing rod 132 is extended from the fixing head 131 and is configured to penetrate the abutment fixing channel 1211 to connect the implant 11 so as to have the abutment 12 fixed to the implant 11. The fixing rod 132 has a rod diameter D32. The rod diameter D32 is smaller than the channel diameter D2 so as to form a tolerance allowable gap G (shown in FIG. 8) between the abutment fixing channel 1211 and the fixing rod 132.

The channel diameter D2 is substantially ranged between 1.05 to 1.3 times the rod diameter D32. For example, if the rod diameter is 2 millimeter, the channel diameter D2 should be ranged from 2.1 to 2.6 millimeter, but the present invention is not so restricted. In addition, the fixing rod 132 has a thread section 1321 at one end thereof away from the fixing head 131, and the fixing element 13 is screw-fixed to the implant fixing hole 113 by using the thread section 1321. That is, the fixing rod 132 is fixed to the implant fixing hole 113.

Figure 7:
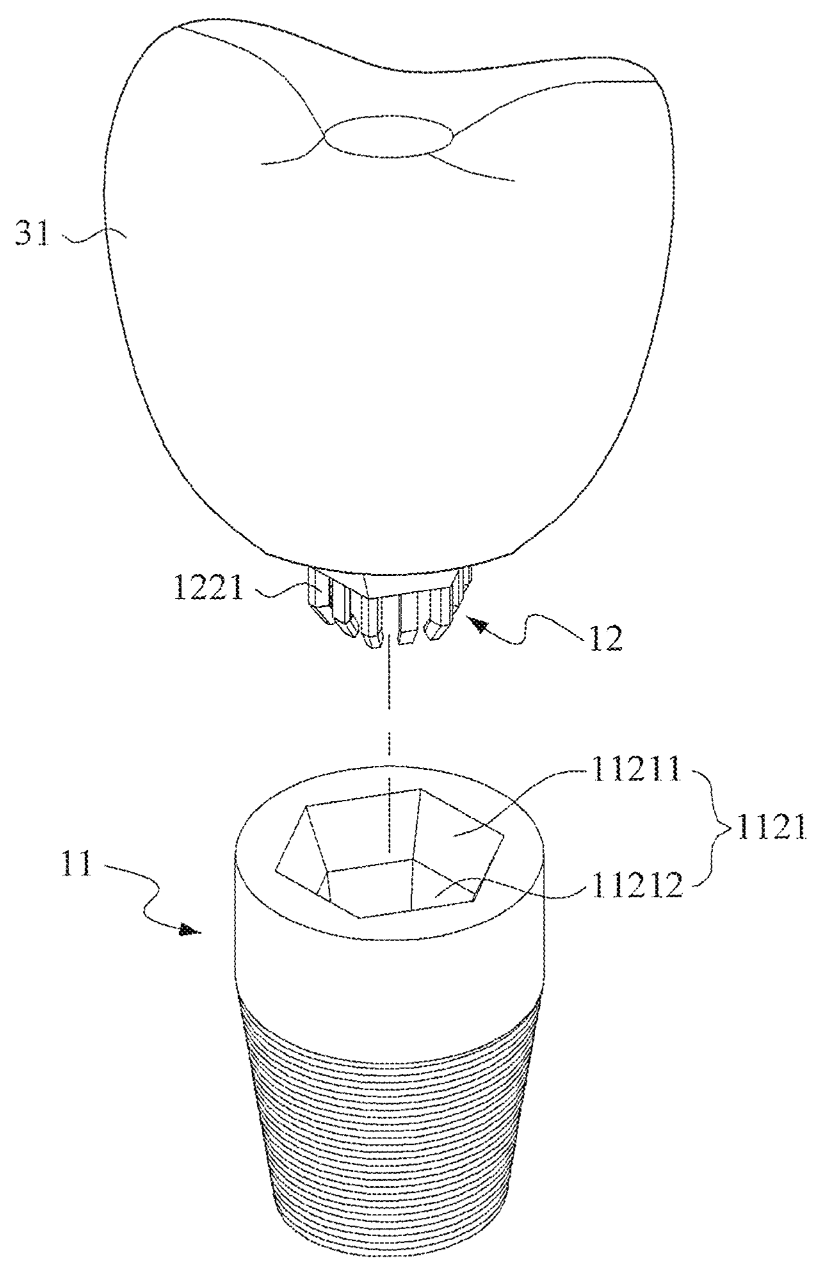
FIG. 7 is a 3D schematic view showing the dental implant assembly together with the crown provided in accordance with the first embodiment of the present invention before the crown is assembled to the dental implant assembly.
Figure 8:
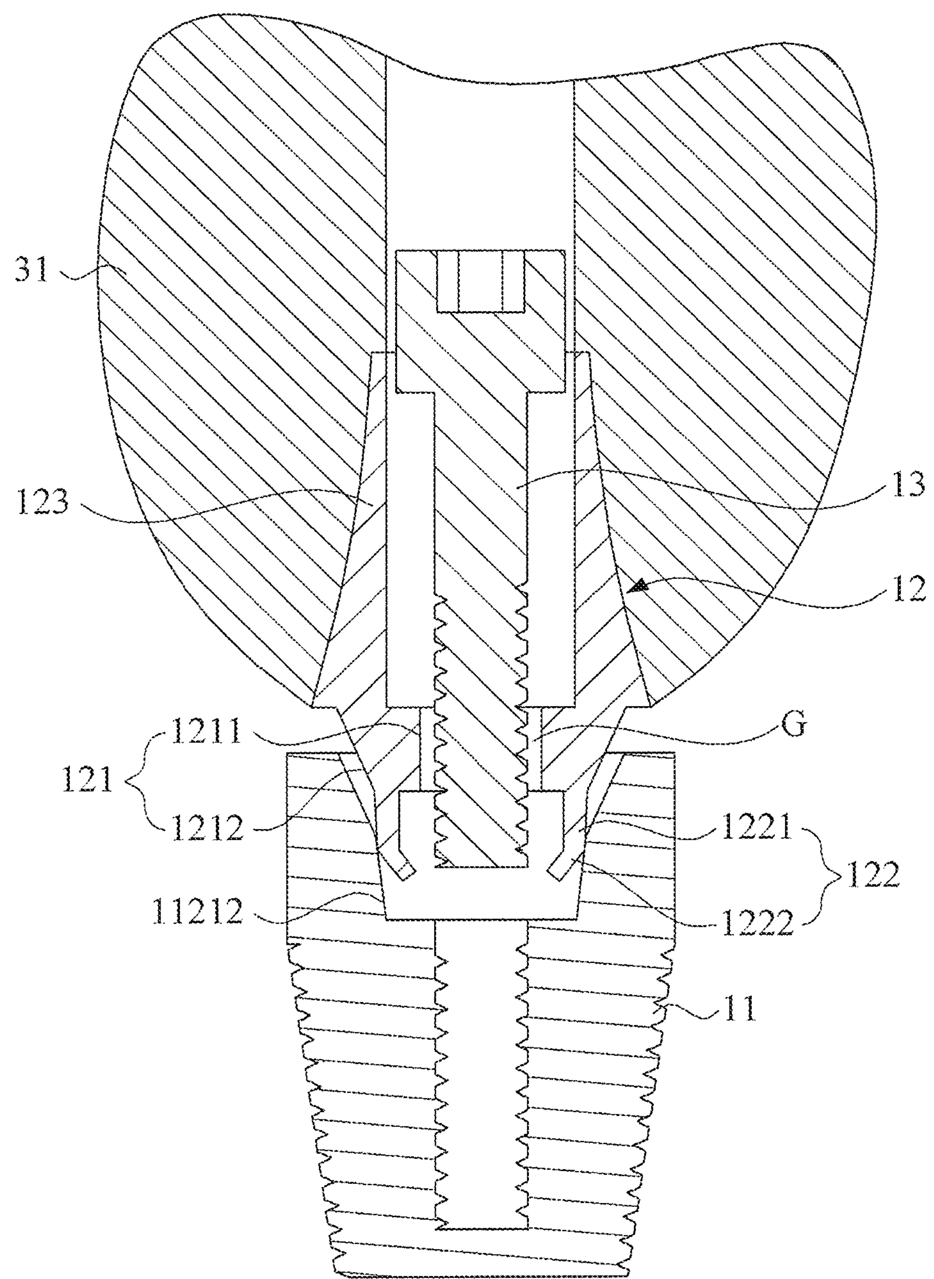
FIG. 8 is a cross-section view showing the dental implant assembly together with the crown provided in accordance with the first embodiment of the present invention before the crown is assembled to the dental implant assembly.
Figure 9:
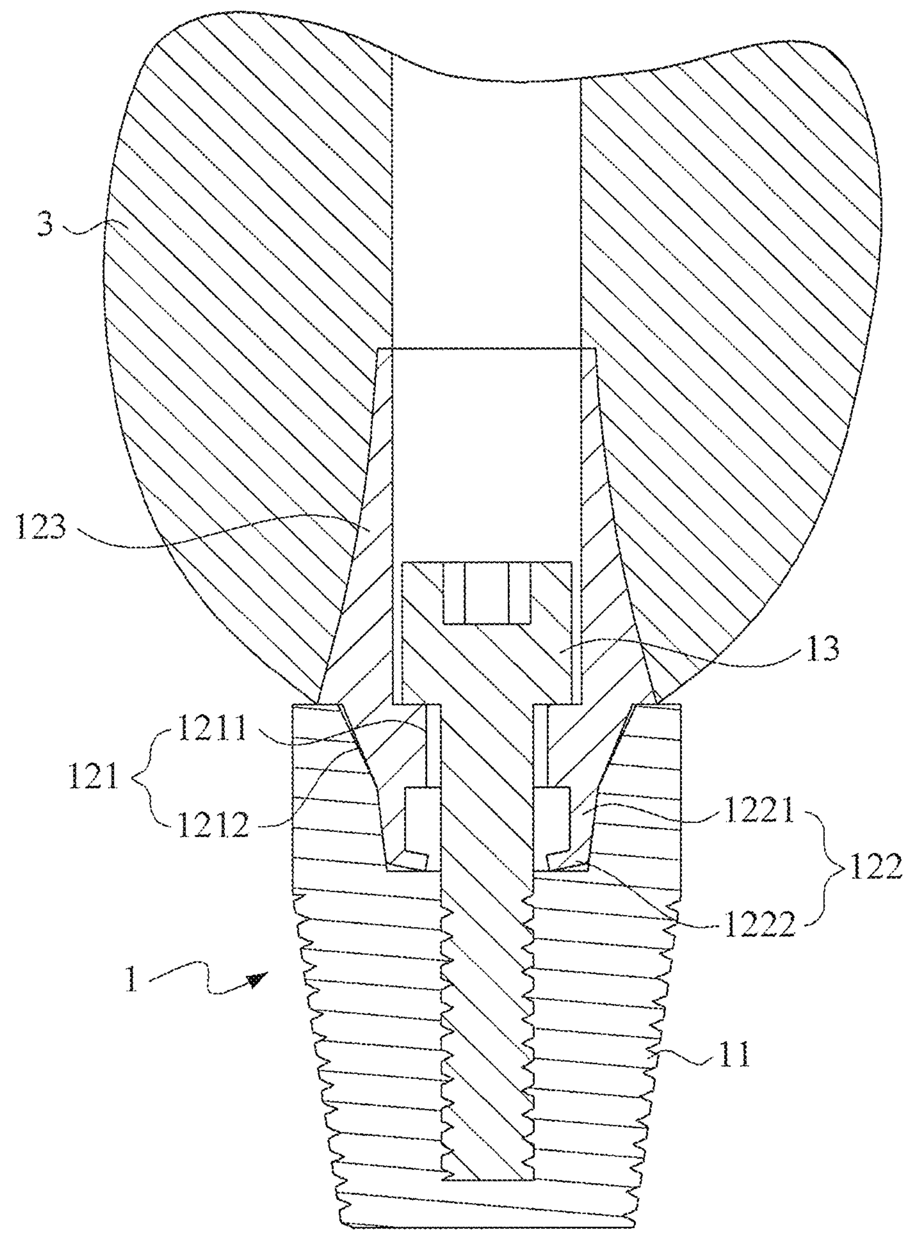
FIG. 9 is a cross-section view showing the dental implant assembly together with the crown provided in accordance with the first embodiment of the present invention after the crown is assembled to the dental implant assembly.

Please refer to FIGS. 7 to 9, wherein FIG. 7 is a 3D schematic view showing the dental implant assembly together with the crown provided in accordance with the first embodiment of the present invention before the crown is assembled to the dental implant assembly; FIG. 8 is a cross-section view showing the dental implant assembly together with the crown provided in accordance with the first embodiment of the present invention before the crown is assembled to the dental implant assembly; and FIG. 9 is a cross-section view showing the dental implant assembly together with the crown provided in accordance with the first embodiment of the present invention after the crown is assembled to the dental implant assembly. As shown, in the ideal condition, a crown 31 would be placed at the crown setting part 123. When the abutment 12 is assembled to the implant 11, the elastic pressing structures 1221 will press against the position-restricting walls 1121 before the tapered position-restricting part 121 because the tilted pressing angle A221 (shown in FIG. 6) is smaller than the tilted position-restricting angle A21 (shown in FIG. 6). To be more precisely, the elastic pressing structure 1221 will press against the pressed portion 11212 to hinder the relative rotation between the abutment 12 and the implant 11.

It is noted that among the elastic pressing structures 1221, there would be six elastic pressing structures 1221 corresponding the six corners of the tapered hexagonal position-restricting trench pressing against the six corners of the pressed portion 11212 to generate the greatest friction force therebetween to hinder the relative rotation between the abutment 12 and the implant 11.

Figure 10:
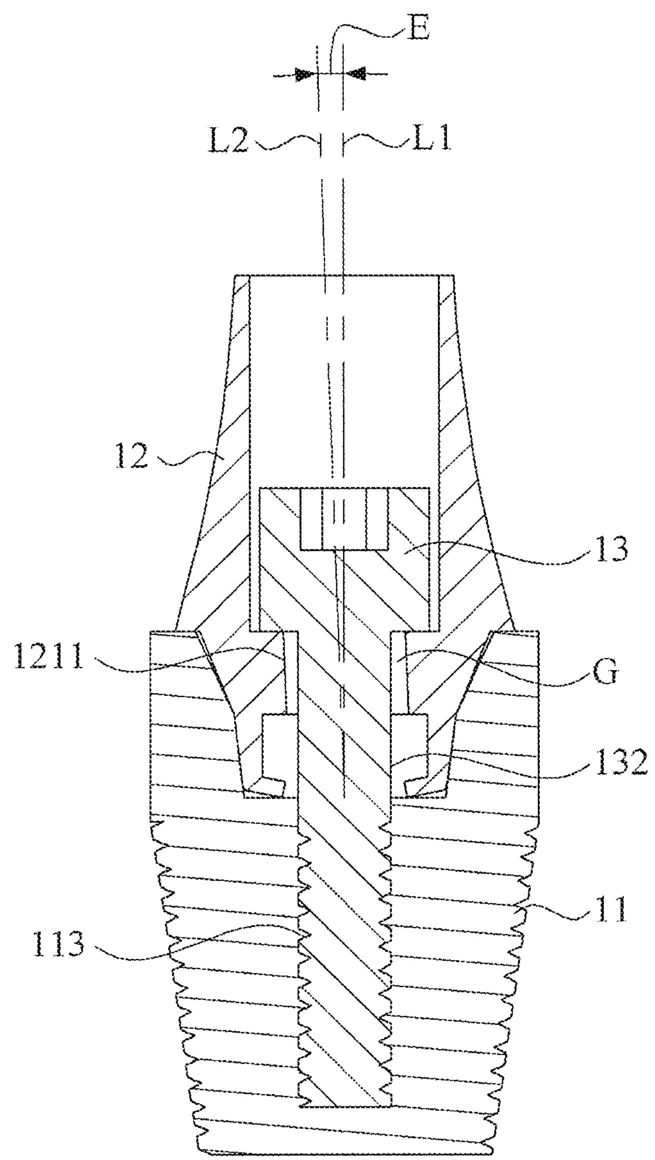
FIG. 10 is a cross-section view showing the dental implant assembly having an abutment fixing channel with an offset error together with the crown provided in accordance with the first embodiment of the present invention after the crown is assembled to the dental implant assembly.

Please refer to FIG. 10, which is a cross-section view showing the dental implant assembly having an abutment fixing channel with an offset error together with the crown provided in accordance with the first embodiment of the present invention after the crown is assembled to the dental implant assembly. In general, it is unpreventable to leave some manufacturing tolerances when manufacturing the implant 11 and the abutment 12. The so-called manufacturing tolerances may also include an offset error E between the implant central axis L1 and the abutment central axis L2. Because of the tolerance allowable gap G, the fixing rod 132 is capable to penetrate the abutment fixing channel 1211 to connect the implant 11 even if the offset error excesses an allowable error range. Some minor positional or angular adjustments can be made to the fixing rod 132 within the tolerance allowable gap G to have the fixing element 13 successfully fixed to the implant fixing hole 113. For example, the tolerance allowable gap G allows the adjustment for the angular deviation of the fixing rod 132 between 0 to 30 degrees. To be more precisely, because of the existence of the tolerance allowable gap G between the abutment fixing channel 1211 and the fixing element 13, the tolerance allowable angle between the axis direction of the fixing rod 132 and the abutment central axis L2 as the fixing rod 132 is placed in the abutment fixing channel 1211 may reach the maximum of 30 degrees. In FIG. 10, the offset error E is due to a minor deviation of the abutment fixing channel 1211 toward the left (i.e. in the counterclockwise direction) when manufacturing the abutment 12. The offset error E can be the angular offset error, i.e. the abutment fixing channel is too much deviated from the abutment central axis L2. In addition, the offset error E can also be the positional offset error, i.e. the abutment fixing channel 1211 is not formed at the ideal position, and the position of the abutment fixing channel 1211 is deviated from the abutment central axis L2.

Figure 11:
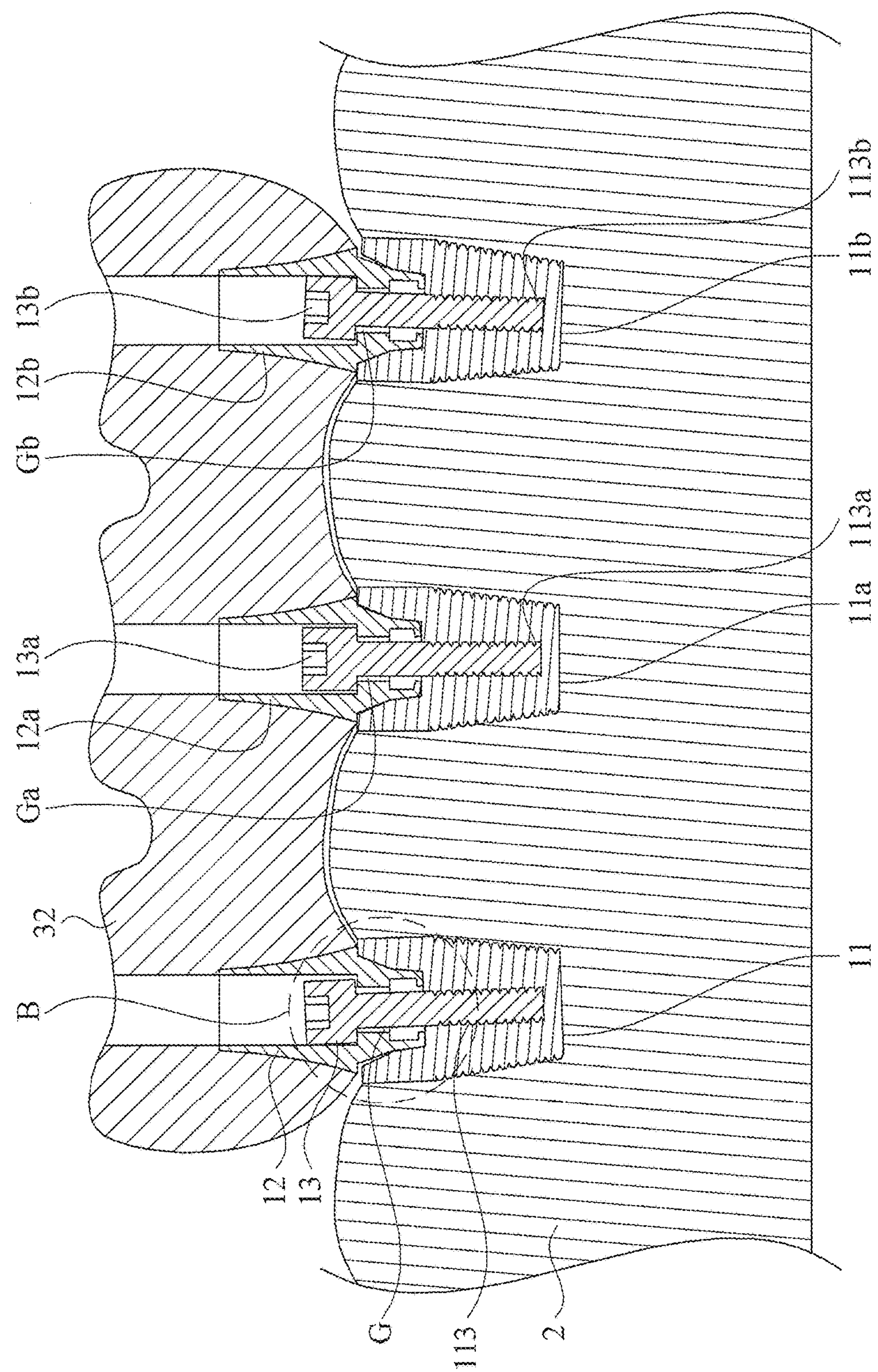
FIG. 11 is a cross-section view of multiple dental implant assemblys with errors together with the dental bridge provided in accordance with second embodiment of the present invention after the assembling.
Figure 12:
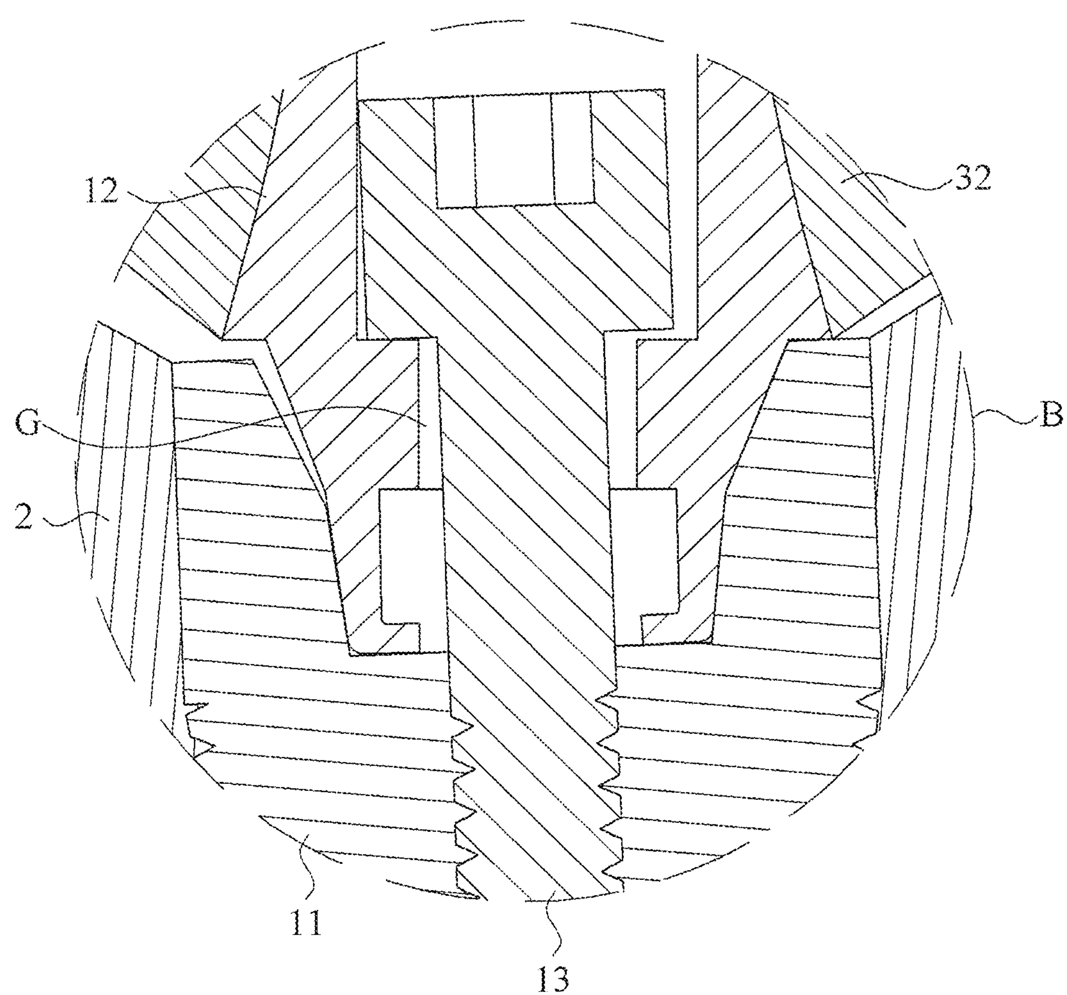
FIG. 12 is an enlarge view of the portion B in FIG. 11.

Please refer to FIGS. 11 and 12, wherein FIG. 11 is a cross-section view of multiple dental implant assemblys with errors together with the dental bridge provided in accordance with second embodiment of the present invention after the assembling, and FIG. 12 is an enlarge view of the portion B in FIG. 11. As shown, when the dentist places the three implants 11, 11*a*, 11*b* as one unit into the alveolar bone 2, human errors are unpreventable such that the three implants 11, 11*a*, 11*b* might not be able to be positioned at the ideal position and tilt angle such that the misalignment issue among the implants would be resulted.

In FIG. 11, these implants 11, 11*a*, 11*b* are unparalleled to each other, the implant 11 has a small deviation toward the counterclockwise direction and the implant 11*b* has a small deviation toward the clockwise direction such that the offset error generated between the implant 11 and the abutment 12 would be different from that generated between the implant 11*b* and the abutment 12*b*. When screw-fixing the three abutments 12, 12*a*, 12*b* jointed by the dental bridge 32 into the implants 11, 11*a*, 11*b*, because of the existence of the tolerance allowable gaps G, Ga, Gb, the tilt angles of the three fixing elements 13, 13*a*, 13*b* can be individually adjusted within the tolerance allowable gaps G, Ga, Gb to have the fixing elements 13, 13*a*, 13*b* successfully fixed into the implant fixing holes 113, 113*a*, 113*b*.

In conclusion, as for the dental implant assembly of single tooth, because of the friction force generated between the elastic pressing structure and the pressed portion, in addition to the matching structures to interfere the relative rotation between the elastic pressing structures and the six corners of the tapered hexagonal position-restricting trench, the relative rotation between the implant and the abutment can be efficiently prevented.

As for the dental implant assembly for multiple teeth, if there are the offset errors between the implant central axis and the abutment central axis, some minor adjustment for the tile angle and the position of the fixing elements can be made within the tolerance allowable gap to have the fixing elements successfully fixed into the implant fixing holes. Accordingly, when implanting the dental implant assembly with multiple teeth, the tolerance allowable gaps of each of the dental implant parts may reduce the influence resulted from the offset errors of individual implants so as to have the fixing elements successfully fixed into the implant fixing holes. In addition, with the elastic deformation of the elastic pressing structures and the guidance of the end elastic pressing structures, the multiple abutments jointed by the dental bridge can be assembled to the multiple implants successfully. Therefore, the multiple abutments jointed by the dental bridge can be fixed into the multiple implants simultaneously, and removed from the multiple implants simultaneously.

The detail description of the above mentioned preferred embodiments is for clarifying the feature and the spirit of the present invention. The present invention should not be limited by any of the exemplary embodiments described herein, but should be defined only in accordance with the following claims and their equivalents. Specifically, those skilled in the art should appreciate that they can readily use the disclosed conception and specific embodiments as a basis for designing or modifying other structures for carrying out the same purposes of the present invention without departing from the scope of the invention as defined by the appended claims.

What is claimed is:

1. A dental implant assembly for placing in an alveolar bone, comprising:

an implant, adapted to be placed in the alveolar bone, and having a tapered position-restricting trench surrounded by a position-restricting wall, wherein the tapered position-restricting trench has an implant central axis;

an abutment, assembled to the implant, and comprising:

a tapered position-restricting part, having an abutment fixing channel along an abutment central axis, and having a tapered position-restricting outer wall substantially engaged with the tapered position-restricting trench, wherein a tilted position-restricting angle is formed between the tapered position-restricting outer wall and the abutment central axis; and an elastic pressing part, comprising a plurality of elastic pressing structures extended from the tapered position-restricting part, wherein a tilted pressing angle formed between the elastic pressing structures and the abutment central axis is smaller than the tilted position-restricting angle; and a fixing element, comprising:

a fixing head, having a head diameter; and a fixing rod, extended from the fixing head for penetrating the abutment fixing channel to connect the implant so as to have the abutment fixed on the implant, and the fixing rod having a rod diameter;

wherein the abutment fixing channel has a channel diameter, the screw head diameter is greater than the channel diameter, and the channel diameter is greater than the rod diameter to generate a tolerance allowable gap between the abutment fixing channel and the fixing rod; when the abutment is assembled to the implant, the elastic pressing structures press against the position-restricting wall before the tapered position-restricting part presses against the position-restricting wall because the tilted pressing angle is smaller than the tilted position-restricting angle such that the elastic pressing structures are elastically deformed to hinder relative rotation between the abutment and the implant; when an offset error exists between the implant central axis and the abutment central axis, the fixing rod penetrates the abutment fixing channel to connect the implant by using the tolerance allowable gap.

2. The dental implant assembly of claim 1, wherein the implant further comprises an implant fixing hole formed from the tapered position-restricting trench extended along the implant central axis, and the fixing rod is fixed in the fixing hole.

3. The dental implant assembly of claim 2, wherein the fixing rod has a thread section at one end thereof away from the fixing head, the implant fixing hole is a screw hole, and the fixing element is screw-fixed to the implant fixing hole by using the thread section.

4. The dental implant assembly of claim 1, wherein the implant further has an implant outer thread section, which is utilized to have the implant screw-fixed to the alveolar bone.

5. The dental implant assembly of claim 1, wherein the elastic pressing part further comprises a plurality of end elastic pressing structures connected to one end of the elastic pressing structures respectively.

6. The dental implant assembly of claim 5, wherein a tilted end structure angle is formed between the end elastic pressing structure and the abutment central axis, and the tilted end structure angle is greater than the tilted pressing angle.

7. The dental implant assembly of claim 1, wherein the channel diameter is ranged from 1.05 to 1.3 times the rod diameter.

8. The dental implant assembly of claim 1, wherein the elastic pressing structures are a plurality of elastic pressing plates spaced apart from each other.

9. The dental implant assembly of claim 1, wherein the position-restricting wall further comprises:

a tapered wall portion, for positioning and locating the tapered position-restricting part; and a pressed portion, pressed by the elastic pressing structure, and a pressed angle formed between the pressed portion and the implant central axis being greater than the tilted pressing angle.

10. The dental implant assembly of claim 9, wherein the tapered wall portion is a cone-shaped position-restricting wall or a polygon-shaped position-restricting wall, and the tapered position-restricting part matching the tapered wall portion is a cone structure or a polygonal pyramid structure.

11. The dental implant assembly of claim 1, wherein the tapered position-restricting trench is a tapered polygonal trench, and the tapered position-restricting part is a tapered polygonal position-restricting part.

* * * * *